(12) United States Patent
Peters et al.

(10) Patent No.: US 7,615,250 B2
(45) Date of Patent: *Nov. 10, 2009

(54) ORGANOALUMINUM PRECURSOR COMPOUNDS

(75) Inventors: David W. Peters, Kingsland, TX (US); Derrik S. Helfer, Decatur, IL (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/020,953

(22) Filed: Jan. 28, 2008

(65) Prior Publication Data

US 2008/0139832 A1 Jun. 12, 2008

Related U.S. Application Data

(60) Division of application No. 11/395,142, filed on Apr. 3, 2006, now Pat. No. 7,348,445, which is a continuation-in-part of application No. 11/341,668, filed on Jan. 30, 2006, now abandoned.

(60) Provisional application No. 60/651,995, filed on Feb. 14, 2005.

(51) Int. Cl.
*C23C 16/00* (2006.01)
*C07F 5/06* (2006.01)

(52) U.S. Cl. .................... 427/248.1; 556/176
(58) Field of Classification Search .............. 427/248.1; 556/176

See application file for complete search history.

(56) References Cited

U.S. PATENT DOCUMENTS 5,880,303 A 3/1999 Choi
6,143,357 A 11/2000 Shin et al.

7,348,445 B2 * 3/2008 Peters et al. ................ 556/176

OTHER PUBLICATIONS

O.T. Beachley, Jr. and K. C. Racette. "Chelation in Organoaluminum-Nitrogen Chemistry." Inorganic Chemistry, vol. 15, No. 9, 1976. pp. 2110-2115.

O.T. Beachley, Jr. and K. C. Racette. "Preparation and Properties of a Neutral, Chelated Four-Coordinate Organoaluminum-Nitrogen Derivative." Inorganic Chemistry, vol. 14, No. 10, 1975. pp. 2534-2537.

Jayaprakash Khanderi, et al. "Ligand Stabilised Dialkyl Aluminium Amides As New Precursors For Aluminium Nitride Thin Films". Journal of Materials Chemistry, 2004, 14, pp. 3210-3214.

Jae E. Park, et al. "Reactions of $AlR_3$ (R=Me, Et) with $H_2NCH_2CH_2NMe_2$: Synthesis and Characterization of Amido- and Imidoalanes." Organometallics 1999, 18. pp. 1059-1067.

* cited by examiner

*Primary Examiner*—Porfirio Nazario Gonzalez
(74) *Attorney, Agent, or Firm*—Iurie A. Schwartz

(57) ABSTRACT

This invention relates to organoaluminum precursor compounds represented by the formula:

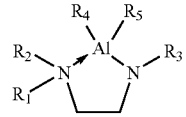

wherein $R_1$, $R_2$, $R_3$ and $R_4$ are the same or different and each represents hydrogen or an alkyl group having from 1 to about 3 carbon atoms, and $R_5$ represents an alkyl group having from 1 to about 3 carbon atoms. This invention also relates to processes for producing the organoaluminum precursor compounds and a method for producing a film or coating from the organoaluminum precursor compounds.

10 Claims, No Drawings

ORGANOALUMINUM PRECURSOR COMPOUNDS

RELATED APPLICATIONS

This application is a divisional of U.S. patent application Ser. No. 11/395,142, filed Apr. 3, 2006, which is a continuation-in-part of U.S. patent application Ser. No. 11/341,668, filed Jan. 30, 2006, which claims priority from provisional U.S. Patent Application Ser. No. 60/651,995, filed Feb. 14, 2005.

FIELD OF THE INVENTION

This invention relates to organoaluminum precursor compounds, processes for producing the organoaluminum precursor compounds, and a method for producing an aluminum or aluminum oxide film or coating from the organoaluminum precursor compounds.

BACKGROUND OF THE INVENTION

Chemical vapor deposition methods are employed to form films of material on substrates such as wafers or other surfaces during the manufacture or processing of semiconductors. In chemical vapor deposition, a chemical vapor deposition precursor, also known as a chemical vapor deposition chemical compound, is decomposed thermally, chemically, photochemically or by plasma activation, to form a thin film having a desired composition. For instance, a vapor phase chemical vapor deposition precursor can be contacted with a substrate that is heated to a temperature higher than the decomposition temperature of the precursor, to form a metal or metal oxide film on the substrate. Preferably, chemical vapor deposition precursors are volatile, heat decomposable and capable of producing uniform films under chemical vapor deposition conditions.

The semiconductor industry is currently considering the use of thin films of various metals for a variety of applications. Many organometallic complexes have been evaluated as potential precursors for the formation of these thin films. A need exists in the industry for developing new compounds and for exploring their potential as chemical vapor deposition precursors for film depositions. Current aluminum precursors for chemical vapor deposition suffer from a number of shortcomings including high viscosity, low stability, pyrophoric nature, low vapor pressure and high cost.

U.S. Pat. No. 5,880,303 discloses volatile, intramolecularly coordinated amido/amine alane complexes of the formula $H_2Al\{(R^1)(R^2)NC_2H_4NR^3\}$ wherein $R^1$, $R^2$ and $R^3$ are each independently hydrogen or alkyl having 1 to 3 carbon atoms. It is stated that these aluminum complexes show high thermal stability and deposit high quality aluminum films at low temperatures. It is also stated that these aluminum complexes are capable of selectively depositing aluminum films on metallic or other electrically conductive substrates. However, these aluminum complexes are either solids or high viscosity liquids at room temperature.

Alumina ($Al_2O_3$ or aluminum oxide) thin films are utilized by the semiconductor industry for applications requiring chemical inertness, high thermal conductivity and radiation resistance. They are used in the manufacture of liquid crystal displays, electroluminescent displays, solar cells, bipolar devices and silicon on insulator (SOI) devices. In addition, alumina is a wear resistant and corrosion resistant coating used in the tool making industry. Most aluminum chemical vapor deposition precursors are pyrophoric which makes them difficult to handle. Those that are not pyrophoric, such as amine-alanes, suffer from short shelf life and high viscosity and low vapor pressure. It would be desirable to develop a non-pyrophoric alumina precursor that had a low viscosity, high vapor pressure and long shelf life.

In developing methods for forming thin films by chemical vapor deposition or atomic layer deposition methods, a need continues to exist for precursors that preferably are liquid at room temperature, have adequate vapor pressure, have appropriate thermal stability (i.e., for chemical vapor deposition will decompose on the heated substrate but not during delivery, and for atomic layer deposition will not decompose thermally but will react when exposed to co-reactant), can form uniform films, and will leave behind very little, if any, undesired impurities (e.g., halides, carbon, etc.). Therefore, a need continues to exist for developing new compounds and for exploring their potential as chemical vapor or atomic layer deposition precursors for film depositions. It would therefore be desirable in the art to provide a precursor that possesses some, or preferably all, of the above characteristics.

SUMMARY OF THE INVENTION

This invention relates to organoaluminum precursor compounds represented by the formula:

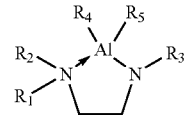

wherein $R_1$, $R_2$, $R_3$ and $R_4$ are the same or different and each represents hydrogen or an alkyl group having from 1 to about 3 carbon atoms, and $R_5$ represents an alkyl group having from 1 to about 3 carbon atoms, provided that when $R_1$ and $R_2$ are methyl and $R_3$ is ethyl, $R_4$ is other than methyl. The organoaluminum precursor compounds employ a chelating amine to protect the aluminum atom which makes the precursor compounds non-pyrophoric.

This invention also relates to a process for the production of an organoaluminum precursor compound represented by the formula

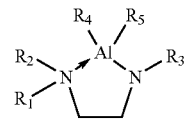

wherein $R_1$, $R_2$, $R_3$ and $R_4$ are the same or different and each represents hydrogen or an alkyl group having from 1 to about 3 carbon atoms, and $R_5$ represents an alkyl group having from 1 to about 3 carbon atoms, which process comprises (i) preparing a first reaction mixture comprising an aluminum source compound and an organodiamine compound in a solvent, (ii) heating the first reaction mixture to reflux for a period of time sufficient to produce a second reaction mixture comprising said organoaluminum precursor compound, and (iii) separating said organoaluminum precursor compound from said second reaction mixture. The organoaluminum precursor compound yield resulting from the process of this invention can be 60% or greater, preferably 75% or greater, and more preferably 90% or greater.

Alternatively, this invention relates to a process for the production of an organoaluminum precursor compound represented by the formula

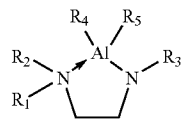

wherein $R_1$, $R_2$, $R_3$ and $R_4$ are the same or different and each represents hydrogen or an alkyl group having from 1 to about 3 carbon atoms, and $R_5$ represents an alkyl group having from 1 to about 3 carbon atoms, which process comprises (i) reacting an organodiamine compound with a base material in the presence of a solvent and under reaction conditions sufficient to produce a first reaction mixture comprising an organodiamine salt compound, (ii) preparing a second reaction mixture by adding an aluminum source compound to said first reaction mixture, (iii) heating the second reaction mixture to reflux for a period of time sufficient to produce a third reaction mixture comprising said organoaluminum precursor compound, and (iv) separating said organoaluminum compound from said third reaction mixture. As with the above process, the organoaluminum compound yield resulting from the process of this invention can be 60% or greater, preferably 75% or greater, and more preferably 90% or greater.

This invention further relates to a method for producing a film, coating or powder by decomposing an organoaluminum precursor compound represented by the formula

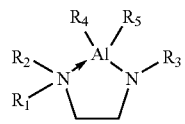

wherein $R_1$, $R_2$, $R_3$ and $R_4$ are the same or different and each represents hydrogen or an alkyl group having from 1 to about 3 carbon atoms, and $R_5$ represents an alkyl group having from 1 to about 3 carbon atoms, provided that when $R_1$ and $R_2$ are methyl and $R_3$ is ethyl, $R_4$ is other than methyl, thereby producing the film, coating or powder. Typically, the decomposing of said organoaluminum precursor compound is thermal, chemical, photochemical or plasma-activated.

This invention also relates to organometallic precursor mixtures comprising (i) an organoaluminum precursor compound represented by the formula

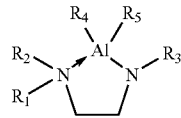

wherein $R_1$, $R_2$, $R_3$ and $R_4$ are the same or different and each represents hydrogen or an alkyl group having from 1 to about 3 carbon atoms, and $R_5$ represents an alkyl group having from 1 to about 3 carbon atoms, and (ii) one or more different organometallic precursor compounds (e.g., a hafnium-containing, tantalum-containing or molybdenum-containing organometallic precursor compound).

This invention relates in part to depositions involving aluminum precursors. The alumina ($Al_2O_3$ or aluminum oxide) thin films of this invention can be utilized by the semiconductor industry for a variety of applications that require chemical inertness, high thermal conductivity and radiation resistance. The alumina films are useful in the manufacture of liquid crystal displays, electroluminescent displays, solar cells, bipolar devices and silicon on insulator (SOI) devices. In addition, the alumina is a wear resistant and corrosion resistant coating useful in the tool making industry.

The organoaluminum precursor compounds of this invention are free flowing liquids that exhibit low viscosity. This makes the organoaluminum precursors easy to use in existing bubbler type chemical dispensing systems. Also, the organoaluminum precursor compounds of this invention have a long shelf life with excellent thermal stability that makes them suitable for chemical vapor deposition and atomic layer deposition, and are non-pyrophoric which makes them easier and safer to handle, ship and store.

The organoaluminum precursors of this invention are liquid at room temperature, i.e., 20° C., and exhibit low viscosity. They can be easily dispensed in existing bubblers and direct liquid injection systems for chemical vapor deposition. Such precursors do not require additional heating for ease of fluid flow. The long shelf life exhibited by the organoaluminum precursors make them economical to scale up production to large batch sizes and customers can store large quantities on site without having to worry about decomposition. Most aluminum containing precursors are pyrophoric. The dangerous nature of pyrophoric chemicals requires special handling, proper training and protective equipment. The organoaluminum precursors of this invention are non-pyrophoric which means they can be handled safely with a minimum of special equipment and training and that they can be shipped by air.

The invention has several other advantages. For example, the method of the invention is useful in generating organoaluminum compound precursors that have varied chemical structures and physical properties. Films (i.e., both aluminum and aluminum oxide films) generated from the organoaluminum compound precursors can be deposited with a short incubation time, and the films deposited from the organoaluminum compound precursors exhibit good smoothness.

DETAILED DESCRIPTION OF THE INVENTION

As indicated above, this invention relates to organoaluminum precursor compounds represented by the formula:

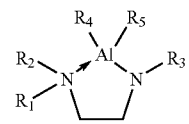

wherein $R_1$, $R_2$, $R_3$ and $R_4$ are the same or different and each represents hydrogen or an alkyl group having from 1 to about 3 carbon atoms, and $R_5$ represents an alkyl group having from 1 to about 3 carbon atoms, provided that when $R_1$ and $R_2$ are methyl and $R_3$ is ethyl, $R_4$ is other than methyl. Illustrative alkyl groups that may be used in $R_1$, $R_2$, $R_3$, $R_4$ and $R_5$ include, for example, methyl, ethyl, n-propyl and isopropyl.

Illustrative organoaluminum precursor compounds of this invention include, for example, dimethylethyl ethylenediamine methylaluminum, trimethyl ethylenediamine dimethylaluminum, triethyl ethylenediamine dimethylaluminum, diethylmethyl ethylenediamine dimethylaluminum, dimethylpropyl ethylenediamine dimethylaluminum, dimethylethyl ethylenediamine diisopropylaluminum, and the like.

As also indicated above, this invention also relates to a process (referred to as "process A" herein) for the production of an organoaluminum precursor compound represented by the formula

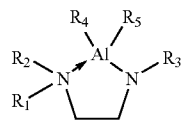

wherein $R_1$, $R_2$, $R_3$ and $R_4$ are the same or different and each represents hydrogen or an alkyl group having from 1 to about 3 carbon atoms, and $R_5$ represents an alkyl group having from 1 to about 3 carbon atoms, which process comprises (i) preparing a first reaction mixture comprising an aluminum source compound and an organodiamine compound in a solvent, (ii) heating the first reaction mixture to reflux for a period of time sufficient to produce a second reaction mixture comprising said organoaluminum precursor compound, and (iii) separating said organoaluminum precursor compound from said second reaction mixture. The organoaluminum precursor compound yield resulting from the process of this invention can be 60% or greater, preferably 75% or greater, and more preferably 90% or greater.

This process A is particularly well-suited for large scale production since it can be conducted using the same equipment, some of the same reagents and process parameters that can easily be adapted to manufacture a wide range of products. The process provides for the synthesis of organoaluminum precursor compounds using a process where all manipulations can be carried out in a single vessel, and which route to the organoaluminum precursor compounds does not require the isolation of an intermediate complex.

The aluminum source compound starting material employed in process A may be selected from a wide variety of compounds known in the art. Illustrative of such aluminum source compounds include, for example, $Me_3Al$, $Me_2AlH$, $Et_3Al$, $Et_2MeAl$, $Et_2AlH$, $^iPr_3Al$, and the like.

The concentration of the aluminum source compound starting material employed in process A can vary over a wide range, and need only be that minimum amount necessary to react with the organodiamine compound and to provide the given aluminum concentration desired to be employed and which will furnish the basis for at least the amount of aluminum necessary for the organoaluminum compounds of this invention. In general, depending on the size of the reaction mixture, aluminum source compound starting material concentrations in the range of from about 1 millimole or less to about 10,000 millimoles or greater, should be sufficient for most processes.

The organodiamine compound starting material employed in process A may be selected from a wide variety of compounds known in the art. Illustrative organodiamine compounds include, for example, dimethylethylethylenediamine, trimethylethylenediamine, triethylethylenediamine, diethylmethylethylenediamine, dimethylpropylethylenediamine, and the like. Preferred organodiamine compound starting materials include dimethylethylethylenediamine, diethylmethylethylenediamine, and the like.

The concentration of the organodiamine compound starting material employed in process A can vary over a wide range, and need only be that minimum amount necessary to react with the base starting material. In general, depending on the size of the reaction mixture, organodiamine compound starting material concentrations in the range of from about 1 millimole or less to about 10,000 millimoles or greater, should be sufficient for most processes.

The solvent employed in process A may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitriles, silicone oils, other aprotic solvents, or mixtures of one or more of the above; more preferably, diethylether, pentanes, or dimethoxyethanes; and most preferably hexanes or toluene. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the reaction of the organodiamine compound with the aluminum source compound in process A, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

As also indicated above, this invention relates to a process (referred to as "process B" herein) for the production of an organoaluminum precursor compound represented by the formula

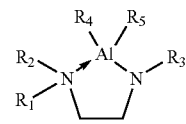

wherein $R_1$, $R_2$, $R_3$ and $R_4$ are the same or different and each represents hydrogen or an alkyl group having from 1 to about 3 carbon atoms, and $R_5$ represents an alkyl group having from 1 to about 3 carbon atoms, which process comprises (i) reacting an organodiamine compound with a base material in the presence of a solvent and under reaction conditions sufficient to produce a first reaction mixture comprising an organodiamine salt compound, (ii) preparing a second reaction mixture by adding an aluminum source compound to said first reaction mixture, (iii) heating the second reaction mixture to reflux for a period of time sufficient to produce a third reaction mixture comprising said organoaluminum precursor compound, and (iv) separating said organoaluminum compound from said third reaction mixture.

The organoaluminum compound yield resulting from the process of this invention can be 60% or greater, preferably 75% or greater, and more preferably 90% or greater. This process B is particularly well-suited for large scale production since it can be conducted using the same equipment, some of the same reagents and process parameters that can easily be adapted to manufacture a wide range of products. The process provides for the synthesis of organoaluminum compounds using a process where all manipulations can be carried out in a single vessel, and which route to the organoaluminum compounds does not require the isolation of an intermediate complex.

The organodiamine compound starting material employed in process B may be selected from a wide variety of compounds known in the art. Illustrative organodiamine compounds include, for example, dimethylethylethylenediamine, trimethylethylenediamine, triethylethylenediamine, diethylmethylethylenediamine, dimethylpropylethylenediamine, and the like. Preferred organodiamine compound starting materials include dimethylethylethylenediamine, diethylmethylethylenediamine, and the like.

The concentration of the organodiamine compound starting material employed in process B can vary over a wide range, and need only be that minimum amount necessary to react with the base starting material. In general, depending on the size of the reaction mixture, organodiamine compound starting material concentrations in the range of from about 1 millimole or less to about 10,000 millimoles or greater, should be sufficient for most processes.

The base starting material employed in process B may be selected from a wide variety of compounds known in the art. Illustrative bases include any base with a pKa greater than about 10, preferably greater than about 20, and more preferably greater than about 25. The base material is preferably n-BuLi, t-BuLi, MeLi, NaH, CaH, and the like.

The concentration of the base starting material employed in process B can vary over a wide range, and need only be that minimum amount necessary to react with the organodiamine compound starting material. In general, depending on the size of the first reaction mixture, base starting material concentrations in the range of from about 1 millimole or less to about 10,000 millimoles or greater, should be sufficient for most processes.

In one embodiment of process B, the organodiamine salt compound may be generated in situ, for example, lithiated organodiamines such as lithiated dimethylethylethylenediamine, lithiated trimethylethylenediamine, lithiated triethylethylenediamine, lithiated diethylmethylethylenediamine, lithiated dimethylpropylethylenediamine, and the like. Generating the organodiamine salt compound in situ in the reaction vessel immediately prior to reaction with the aluminum source compound is beneficial from a purity standpoint by eliminating the need to isolate and handle any reactive solids. It is also less expensive.

With the in situ generated organodiamine salt compound in place, addition of the aluminum source compound, e.g., $Me_2AlCl$, can be performed through solid addition, or in some cases more conveniently as a solvent solution or slurry. Although certain aluminum source compounds are moisture sensitive and are used under an inert atmosphere such as nitrogen, it is generally to a much lower degree than the organodiamine salt compounds, for example, lithiated dimethylethylethylenediamine and the like. Furthermore, many aluminum source compounds are denser and easier to transfer.

The organodiamine salt compounds of process B that are prepared from the reaction of the organodiamine compound starting material and the base starting material may be selected from a wide variety of compounds. Illustrative organodiamine salt compounds include, for example, lithiated dimethylethylethylenediamine, lithiated trimethylethylenediamine, lithiated triethylethylenediamine, lithiated diethylmethylethylenediamine, lithiated dimethylpropylethylenediamine, and the like.

The concentration of the organodiamine salt compounds employed in process B can vary over a wide range, and need only be that minimum amount necessary to react with the aluminum source compounds to give the organoaluminum compounds of this invention. In general, depending on the size of the reaction mixture, organodiamine salt compound concentrations in the range of from about 1 millimole or less to about 10,000 millimoles or greater, should be sufficient for most processes.

The aluminum source compound starting material employed in process B may be selected from a wide variety of compounds known in the art. Illustrative of such aluminum source compounds include, for example, $Me_2AlCl$, $Me_2AlBr$, $Me_2AlF$, $Et_2AlCl$, $EtMeAlCl$, $^iPr_2AlCl$, and the like.

The concentration of the aluminum source compound starting material employed in process B can vary over a wide range, and need only be that minimum amount necessary to react with the organodiamine salt compound and to provide the given aluminum concentration desired to be employed and which will furnish the basis for at least the amount of aluminum necessary for the organoaluminum compounds of this invention. In general, depending on the size of the reaction mixture, aluminum source compound starting material concentrations in the range of from about 1 millimole or less to about 10,000 millimoles or greater, should be sufficient for most processes.

The solvent employed in process B may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitriles, silicone oils, other aprotic solvents, or mixtures of one or more of the above; more preferably, diethylether, pentanes, or dimethoxyethanes; and most preferably hexanes or toluene. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the reaction of the base starting material with the organodiamine compound in process B, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

Reaction conditions for the reaction of the organodiamine salt compound with the aluminum source compound in process B, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps. In the embodiment of this invention which is carried out in a single pot, the organodiamine salt compound is not separated from the first reaction mixture prior to reacting with the aluminum source compound. In a preferred embodiment, the aluminum source compound is added to the first reaction mixture at ambient temperature or at a temperature greater than ambient temperature.

The processes of the invention are preferably useful in generating organoaluminum compound precursors that have varied chemical structures and physical properties. A wide variety of reaction materials may be employed in the processes of this invention.

For organoaluminum precursor compounds prepared by the processes of this invention, purification can occur through recrystallization, more preferably through extraction of reaction residue (e.g., hexane) and chromatography, and most preferably through sublimation and distillation.

Those skilled in the art will recognize that numerous changes may be made to the method described in detail herein, without departing in scope or spirit from the present invention as more particularly defined in the claims below.

Examples of techniques that can be employed to characterize the organoaluminum precursor compounds formed by the synthetic methods described above include, but are not limited to, analytical gas chromatography, nuclear magnetic resonance, thermogravimetric analysis, inductively coupled plasma mass spectrometry, differential scanning calorimetry, vapor pressure and viscosity measurements.

Relative vapor pressures, or relative volatility, of organoaluminum compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

The organoaluminum compound precursors described herein are preferably liquid at room temperature, i.e., 20° C., and are well suited for preparing in-situ powders and coatings. For instance, a liquid organoaluminum compound precursor can be applied to a substrate and then heated to a temperature sufficient to decompose the precursor, thereby forming an aluminum or aluminum oxide coating on the substrate. Applying a liquid precursor to the substrate can be by painting, spraying, dipping or by other techniques known in the art. Heating can be conducted in an oven, with a heat gun, by electrically heating the substrate, or by other means, as known in the art. A layered coating can be obtained by applying an organoaluminum compound precursor, and heating and decomposing it, thereby forming a first layer, followed by at least one other coating with the same or different precursors, and heating.

Liquid organoaluminum compound precursors such as described above also can be atomized and sprayed onto a substrate. Atomization and spraying means, such as nozzles, nebulizers and others, that can be employed are known in the art.

In preferred embodiments of the invention, an organoaluminum compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic compound precursor, such as described above, also can be employed in a given process.

As indicated above, this invention relates to organometallic precursor mixtures comprising (i) an organoaluminum precursor compound represented by the formula

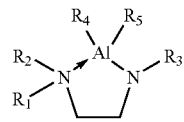

wherein $R_1$, $R_2$, $R_3$ and $R_4$ are the same or different and each represents hydrogen or an alkyl group having from 1 to about 3 carbon atoms, and $R_5$ represents an alkyl group having from 1 to about 3 carbon atoms, and (ii) one or more different organometallic precursor compounds (e.g., a hafnium-containing, tantalum-containing or molybdenum-containing organometallic precursor compound).

Deposition can be conducted in the presence of other gas phase components. In an embodiment of the invention, film deposition is conducted in the presence of at least one non-reactive carrier gas. Examples of non-reactive gases include inert gases, e.g., nitrogen, argon, helium, as well as other gases that do not react with the organoaluminum compound precursor under process conditions. In other embodiments, film deposition is conducted in the presence of at least one reactive gas. Some of the reactive gases that can be employed include but are not limited to hydrazine, oxygen, hydrogen, air, oxygen-enriched air, ozone ($O_3$), nitrous oxide ($N_2O$), water vapor, organic vapors, ammonia and others. As known in the art, the presence of an oxidizing gas, such as, for example, air, oxygen, oxygen-enriched air, $O_3$, $N_2O$ or a vapor of an oxidizing organic compound, favors the formation of a metal oxide film.

As indicated above, this invention also relates in part to a method for producing a film, coating or powder. The method includes the step of decomposing at least one organoaluminum compound precursor, thereby producing the film, coating or powder, as further described below.

Deposition methods described herein can be conducted to form a film, powder or coating that includes a single metal or a film, powder or coating that includes a single metal oxide. Mixed films, powders or coatings also can be deposited, for instance mixed metal oxide films. A mixed metal oxide film can be formed, for example, by employing several organometallic precursors, at least one of which being selected from the organoaluminum compounds described above.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of this invention, for instance, can be considered for fabricating metal electrodes, in particular as n-channel metal electrodes in logic, as capacitor electrodes for DRAM applications, and as dielectric materials.

The method also is suited for preparing layered films, wherein at least two of the layers differ in phase or composition. Examples of layered film include metal-insulator-semiconductor, and metal-insulator-metal.

In an embodiment, the invention is directed to a method that includes the step of decomposing vapor of an organoaluminum compound precursor described above, thermally, chemically, photochemically or by plasma activation, thereby forming a film on a substrate. For instance, vapor generated by the compound is contacted with a substrate having a temperature sufficient to cause the organoaluminum compound to decompose and form a film on the substrate.

The organoaluminum compound precursors can be employed in chemical vapor deposition or, more specifically, in metalorganic chemical vapor deposition processes known in the art. For instance, the organoaluminum compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organoaluminum compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The method of the invention can be conducted in various chemical vapor deposition reactors, such as, for instance, hot or cold-wall reactors, plasma-assisted, beam-assisted or laser-assisted reactors, as known in the art.

Examples of substrates that can be coated employing the method of the invention include solid substrates such as metal substrates, e.g., Al, Ni, Ti, Co, Pt, Ta; metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); barrier materials, e.g., TiN, TaN; or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The method of this invention can be conducted to deposit a film on a substrate that has a smooth, flat surface. In an embodiment, the method is conducted to deposit a film on a substrate used in wafer manufacturing or processing. For instance, the method can be conducted to deposit a film on patterned substrates that include features such as trenches, holes or vias. Furthermore, the method of the invention also can be integrated with other steps in wafer manufacturing or processing, e.g., masking, etching and others.

Chemical vapor deposition films can be deposited to a desired thickness. For example, films formed can be less than 1 micron thick, preferably less than 500 nanometers and more preferably less than 200 nanometers thick. Films that are less than 50 nanometers thick, for instance, films that have a thickness between about 0.1 and about 20 nanometers, also can be produced.

Organoaluminum compound precursors described above also can be employed in the method of the invention to form films by atomic layer deposition (ALD) or atomic layer nucleation (ALN) techniques, during which a substrate is exposed to alternate pulses of precursor, oxidizer and inert gas streams. Sequential layer deposition techniques are described, for example, in U.S. Pat. No. 6,287,965 and in U.S. Pat. No. 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. milliseconds) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

The method of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organoaluminum compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form an aluminum or aluminum oxide film on the substrate. The reaction also generates organic material from the precursor. The organic material is solubilized by the solvent fluid and easily removed away from the substrate. Aluminum oxide films also can be formed, for example by using an oxidizing gas.

In an example, the deposition process is conducted in a reaction chamber that houses one or more substrates. The substrates are heated to the desired temperature by heating the entire chamber, for instance, by means of a furnace. Vapor of the organoaluminum compound can be produced, for example, by applying a vacuum to the chamber. For low boiling compounds, the chamber can be hot enough to cause vaporization of the compound. As the vapor contacts the heated substrate surface, it decomposes and forms an aluminum or aluminum oxide film. As described above, an organoaluminum compound precursor can be used alone or in combination with one or more components, such as, for example, other organometallic precursors, inert carrier gases or reactive gases.

In a system that can be used in producing films by the method of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organoaluminum compound precursors described above can be employed to produce films that include a single aluminum or a film that includes a single aluminum oxide. Mixed films also can be deposited, for instance mixed metal oxide films. Such films are produced, for example, by employing several organometallic precursors. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

Various modifications and variations of this invention will be obvious to a worker skilled in the art and it is to be understood that such modifications and variations are to be included within the purview of this application and the spirit and scope of the claims.

EXAMPLE 1

Synthesis of Trimethyl Ethylenediamine Dimethylaluminum (TMEDDMA)

a. Under an inert atmosphere of nitrogen, 5 milliliters of trimethylaluminum in 30 milliliters of anhydrous toluene are cooled to 0° C. To this solution is added, drop wise, 8.5 milliliters of trimethylethylenediamine. The reaction is heated to reflux for 2 hours and is stirred at room temperature for 12 more hours. The solvent is removed under reduced pressure and the remaining product is distilled under reduced pressure. The light cuts from the distillation are discarded leaving only pure TMEDDMA.

EXAMPLE 2

Alternate Synthesis of TMEDDMA

Under an inert atmosphere of nitrogen, 22 milliliters of trimethylethylenediamine in 250 milliliters of hexanes are cooled to 0° C. 51 milliliters of n-butyllithium are added to the solution in a drop wise manner. The solution is allowed to warm to room temperature and is stirred for 12 hours yielding a yellow liquid and colorless solid. This solution is again cooled to 0° C. and 9 milliliters of $Me_2AlCl$ are added drop wise. The solution is allowed to warm to room temperature and is stirred for 16 hours. The solid is removed from the solution via filtration and solvent is removed under reduced pressure. An NMR of the solution shows TMEDDMA along with impurities.

EXAMPLE 3

Thermal Stability of TMEDDMA

The thermal stability of TMEDDMA is evaluated by exposing a silicon wafer to a mixture containing only argon and TMEDDMA vapors at approximately 330° C. The TMEDDMA is evaporated at 40° C., using 100 standard cubic centimeters of argon. The TMEDDMA vaporizer is maintained at 50 Torr, using a needle valve between the vaporizer and the deposition reactor. The equipment useful in this experiment is described in J. Atwood, D. C. Hoth, D. A. Moreno, C. A. Hoover, S. H. Meiere, D. M. Thompson, G. B. Piotrowski, M. M. Litwin, J. Peck, *Electrochemical Society Proceedings* 2003-08, (2003) 847. The deposition reactor is maintained at 5 Torr. The material exiting the TMEDDMA vaporizer is combined with an additional 360 standard cubic centimeters of argon (i.e., total flow of mixture is 460 standard cubic centimeters) prior to wafer exposure. No material is deposited after the wafer is exposed to this mixture for 15 minutes. This indicates that the thermal stability of TMEDDMA at 330° C. is sufficient for use in an atomic layer deposition process and should be self-limiting.

EXAMPLE 4

Atomic Layer Deposition of Alumina from TMEDDMA

In order to determine the ability of TMEDDMA to be used in an atomic layer deposition process, wafers are exposed to alternating pulses of TMEDDMA and $H_2O$ separated by argon purge. Aluminum oxide films are deposited at approximately 330° C. The atomic layer deposition cycle consists of 4 steps: (1) TMEDDMA and argon, (2) argon purge, (3) $H_2O$ and argon, and (4) argon purge. The duration of the 4 steps is 10/20/10/20 seconds respectively.

Film growth is monitored in-situ using a dual wavelength pyrometer. A pyrometer uses emitted radiation to determine temperature. Thin film growth introduces constructive and destructive interference to this radiation, and results in a pattern of oscillations when tracking the apparent wafer temperature. These oscillations (increase or decrease) in temperature can be used to detect film growth in-situ. Oscillation in the temperature measured by the pyrometer is verified during the 4 step atomic layer deposition process using TMEDDMA and $H_2O$ described above. By eliminating $H_2O$ during the third step (argon only), the oscillations cease (i.e., temperature no longer increases or decreases). This indicates that the process is self-limiting.

The results show TMEDDMA is a suitable candidate for depositing aluminum oxide films by atomic layer deposition. The results imply that TMEDDMA could also be used to deposit aluminum oxide by a chemical vapor deposition process as well. Suitable oxygen-containing coreactants for the deposition of aluminum oxide using TMEDDMA in either a chemical vapor deposition or atomic layer deposition process include $H_2O$, oxygen, ozone, and alcohols.

The invention claimed is:

1. A method for producing a film, coating or powder by decomposing a mixture comprising (i) an organoaluminum precursor compound represented by the formula

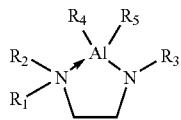

wherein $R_1$, $R_2$, $R_3$ and $R_4$ are the same or different and each represents hydrogen or an alkyl group having from 1 to about 3 carbon atoms, and $R_5$ represents an alkyl group having from 1 to about 3 carbon atoms, and (ii) one or more different organometallic precursor compounds; thereby producing the film, coating or powder.

2. The method of claim 1 wherein the decomposing of said mixture is thermal, chemical, photochemical or plasma-activated.

3. The method of claim 2 wherein said mixture is vaporized and the vapor is directed into a deposition reactor housing a substrate.

4. The method of claim 3 wherein said substrate is comprised of a material selected from the group consisting of a metal, a metal silicide, a semiconductor, an insulator and a barrier material.

5. The method of claim 4 wherein said substrate is a patterned wafer.

6. The method of claim 1 wherein said film, coating or powder is produced by a gas phase deposition.

7. The method of claim 1 wherein the organoaluminum precursor compound is a liquid at 20° C.

8. The method of claim 1 wherein said one or more other organometallic precursor compounds are selected from a hafnium-containing, tantalum-containing or molybdenum-containing organometallic precursor compound.

9. The method of claim 1 wherein $R_1$, $R_2$, $R_3$ and $R_4$ are the same or different and each represents hydrogen, methyl, ethyl, n-propyl or isopropyl, and $R_5$ represents methyl, ethyl, n-propyl or isopropyl.

10. The method of claim 1 wherein the organoaluminum precursor compound is selected from dimethylethyl ethylenediamine methylaluminum, trimethyl ethylenediamine dimethylaluminum, triethyl ethylenediamine dimethylaluminum, diethylmethyl ethylenediamine dimethylaluminum, dimethylpropyl ethylenediamine dimethylaluminum, and dimethylethyl ethylenediamine diisopropylaluminum.

* * * * *